United States Patent
Purcell

(10) Patent No.: US 7,316,929 B2
(45) Date of Patent: Jan. 8, 2008

(54) AUTO-CALIBRATION LABEL AND APPARATUS COMPRISING SAME

(75) Inventor: D. Glenn Purcell, Edwardsburg, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 765 days.

(21) Appl. No.: 10/635,504

(22) Filed: Aug. 7, 2003

(65) Prior Publication Data

US 2004/0047764 A1 Mar. 11, 2004

Related U.S. Application Data

(60) Provisional application No. 60/409,331, filed on Sep. 10, 2002.

(51) Int. Cl.
*G01N 31/00* (2006.01)

(52) U.S. Cl. .................... 436/8; 436/149; 422/58; 422/68.1; 422/99; 422/98; 422/82.01

(58) Field of Classification Search ............... 422/58, 422/61, 68.1, 99, 82.01, 98; 436/8, 14, 63, 436/95, 149

See application file for complete search history.

(56) References Cited

U.S. PATENT DOCUMENTS

| | | | | |
|---|---|---|---|---|
| 5,266,179 A | | 11/1993 | Nankai et al. ............... 204/401 |
| 5,575,403 A | * | 11/1996 | Charlton et al. ............... 221/31 |
| 5,630,986 A | * | 5/1997 | Charlton et al. ............... 422/64 |
| 5,738,244 A | * | 4/1998 | Charlton et al. ............... 221/26 |
| 5,810,199 A | * | 9/1998 | Charlton et al. ............... 221/31 |
| 5,854,074 A | * | 12/1998 | Charlton et al. ............... 436/46 |
| 5,856,195 A | | 1/1999 | Charlton et al. ............... 436/50 |

FOREIGN PATENT DOCUMENTS

| EP | 1024358 | * | 8/2000 |
|---|---|---|---|
| JP | 2000-19147 | * | 1/2000 |

* cited by examiner

*Primary Examiner*—Maureen M. Wallenhorst
(74) *Attorney, Agent, or Firm*—Nixon Peabody LLP

(57) ABSTRACT

An auto-calibration label for use with one or more sensing instruments. The label includes first and second encoded calibration information. The second encoded calibration information may correspond to a different instrument than the first encoded calibration information. The second encoded information may also be used to provide additional calibration information for use with the first instrument. The label may be removably attached to a sensor package including a plurality of sensors. A first conductive ink pattern is disposed on the label to define the first encoded calibration information. The first conductive ink pattern is disposed contemporaneously with or without a portion of a second conductive ink pattern defining the second encoded calibration information. An insulating layer is disposed on the first pattern. The second ink pattern is disposed on the insulating layer. The first pattern is operable with the first instrument, not the second instrument. The second pattern is operable with the second instrument, not the first instrument.

45 Claims, 2 Drawing Sheets

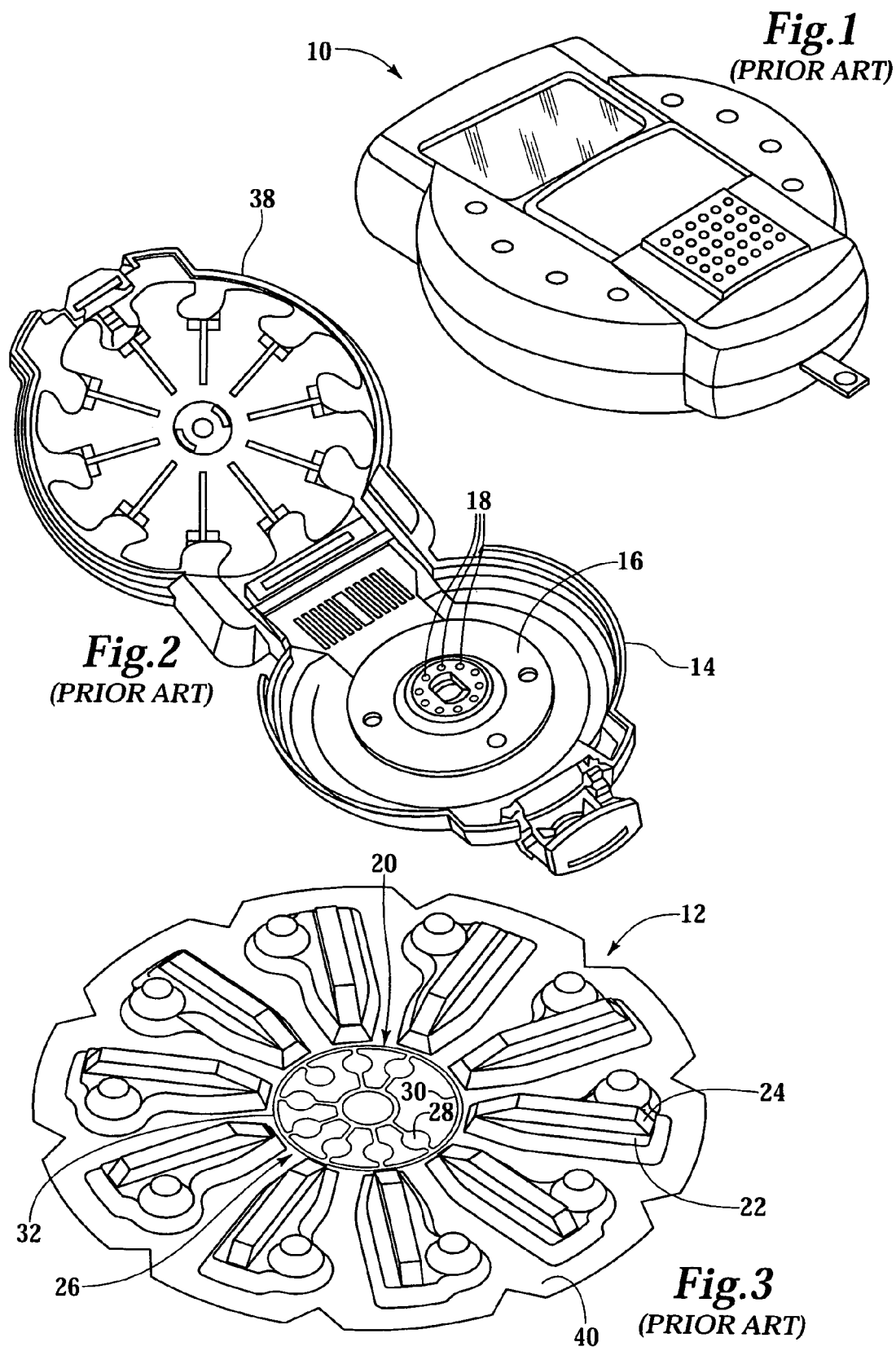

AUTO-CALIBRATION LABEL AND APPARATUS COMPRISING SAME

CROSS-REFERENCE TO RELATED APPLICATION

This application claims benefit to U.S. Provisional Application No. 60/409,331, filed on Sep. 10, 2002.

FIELD OF THE INVENTION

The present invention generally relates to sensor instruments, and, more particularly, to a new and improved method and apparatus for calibrating a sensor instrument. Particular embodiments relate to sensor packages for use with an analyte monitoring instrument.

BACKGROUND OF THE INVENTION

The field of clinical chemistry is concerned with the detection and quantitation of various substances in body material, typically body fluids such as blood, urine or saliva. In one important aspect of this field, the concentration of naturally occurring substances, such as cholesterol or glucose, in an individual's blood is determined. One of the most frequently used analytical devices in clinical chemistry for determining the concentration of an analyte in a fluid sample is the test sensor. Upon contacting the test sensor with the fluid sample, certain reagents incorporated into the sensor react with the analyte whose concentration is being sought to provide a detectable signal. The signal may be a change in color as in the case of a calorimetric sensor or a change in current or potential as in the case of an electrochemical system.

For a particular class of electrochemical sensors, e.g., amperometric sensors, the detected current is proportional to the concentration of the analyte in the fluid sample being tested. Those systems which employ an enzyme in the reagent system may be referred to as biosensors since they rely on the interaction of the enzyme (a biological material) with the analyte to provide the detectable response. This response, whether it be a change in color or in current or in potential, is typically measured by a meter, into which the sensor is inserted. The meter typically provides a readout of the analyte concentration such as by means of a LCD system.

Glucose is one such analyte that is of particular importance. The determination of glucose in blood is of great importance to diabetic individuals who must frequently check the level of glucose in connection with regulating the glucose intake in their diets and their medications. While the remainder of the disclosure herein will be directed towards the determination of glucose in blood, it is to be understood that the procedure and apparatus of this invention can be used for the determination of other analytes in other body fluids or even non-fluid body materials such as the detection of concealed blood in fecal material upon selection of the appropriate enzyme. In addition such sensors can be used in, for example, testing for meat spoilage or foreign substances in well water.

Diagnostic systems, such as blood glucose measuring systems, typically calculate the actual glucose value based on a measured output and the known reactivity of the reagent sensing element used to perform the test. The latter information can be given to the user in several forms including a number or character that they enter into the instrument. One method included the use of an element that is similar to a test sensor but which is capable of being recognized as a calibration element by the instrument. The test element's information is read by the instrument or a memory element that is plugged into the instrument's microprocessor board for directly reading the test element.

Various arrangements have been used to provide lot calibration information of sensors, for example, to the instrument. A basic method requires the user to enter a code number which the instrument can use to retrieve calibration constants from a lookup table. The transfer of information, for example, may comprise use of a resistor whose resistance value can be measured by the instrument. Further detail concerning use of a resistor is found in U.S. Pat. No. 5,266,179, which is incorporated herein by reference in its entirety. From the resistance value the calibration constants are recovered from the lookup table.

Problems associated with the prior art are discussed and addressed in U.S. Pat. No. 5,856,195 (the '195 patent), which is commonly assigned and incorporated herein by reference in its entirety. The success of sensing meters designed in accordance with the '195 patent has lead to the development of improved sensing meters and improved sensors. For example, existing sensing meters analyze the sample for a predetermined length of time equal to approximately 30 seconds. New improved sensing meters are not restricted to fixed analysis lengths of 30 seconds.

As taught in the '195 patent, the sensing meters should be calibrated to operate appropriately with the sensors to achieve accurate test results. As the new improved sensing meters are being put to use in the field, the former, older, sensing meters will still be used for an unknown period of time. If calibration codes adapted for characteristics of the new improved meters are used in older meters, test results are likely to be inaccurate. Thus, it would be desirable to avoid such inaccurate test results.

SUMMARY OF THE INVENTION

One embodiment comprises providing along with the sensing package, also referred to as a blister pack, calibration codes for the old meters as well as calibration codes for the new meters. One method of providing calibration codes for a plurality of meters with the sensor package (also sensing package) is to provide a plurality of auto-calibration labels that are attachable to the sensor package. Each of the plurality of auto-calibration labels is encoded with calibration information corresponding to one of a plurality of different sensing meters. The user of the sensing meter is thereby provided with a selection of labels from which to select the label corresponding to the sensing meter to be used. The label is then, in one embodiment, attached to the blister pack. The blister pack is then used as taught in the '195 patent, wherein the sensing meter utilizes the label to auto-calibrate.

Another method of providing calibration data to the instrument may be combined with the above method or used as an alternative to the above method. In this method calibration codes corresponding to a plurality of different devices are provided on a single label to form, for example, a dual auto-calibration label. By the same method a greater number of sensor calibration codes corresponding to a single type of meter can be provided. For example, where a label carries 8 codes corresponding to 8 sensors, another set of 8 codes corresponding the same 8 sensors, or a different set of 8 sensors, can be added to the label to double the total number of sensor codes provided. Combining these two examples, it will be seen that 16 calibration codes can be provided where each code is unique to a particular sensor and a particular instrument using the sensor. Such an arrangement is particularly useful with reusable sensors adapted for use in a variety of instruments.

In a typical prior art embodiment, a disposable blister package (sensor package) is provided with encoded calibration information corresponding to one instrument and one sensor, where all the sensors in the package have substantially the same calibration characteristic. Thus, a single calibration code is utilized by the meter to auto-calibrate the meter to use, in due course, all the sensors in the package.

An improvement over the prior art, and described with respect to the above example, comprises providing encoded calibration information corresponding to an earlier generation meter and encoded calibration information corresponding to a newer generation meter. In a preferred embodiment, the encoded information is provided on a single auto-calibration label. The encoded information corresponding to the first instrument is defined with a first conductive ink pattern and the encoded information corresponding to the second instrument is defined with a second conductive ink pattern. The second pattern is overlays the first pattern and is preferably isolated from the first pattern.

Where the patterns are formed with screen printing techniques, it is often desirable to reduce the total number of passes to form the label. One method for reducing the total number of passes comprises printing the first pattern and an outer ring of the second pattern in the first printing pass. To help isolate the patterns, the outer ring of the second pattern may be larger than the outer ring of the first pattern and be positioned to not contact the first pattern. A second printing pass lays down an insulating layer, preferably an insulating layer containing a dielectric. A third printing pass lays down the remainder of the second pattern. The first and second patterns are thus layered and isolated from each other.

The patterns may be formed with both inner and outer circles connected by traces. The patterns are formed with predetermined electrical contacts, also referred to as pads, that couple each pattern to the corresponding instrument. The arrangement of the patterns and the layer prevent the first instrument from utilizing the second pattern to auto-calibrate and likewise prevent the second instrument from utilizing the first pattern to auto-calibrate.

OBJECT OF THE INVENTION

An object of the invention is to overcome problems associated with modifying and upgrading components in systems where reverse compatibility is desired.

Another object of the invention is to reduce injuries to individuals resulting from inaccurate sample analysis, e.g., inaccurate glucose concentration readings.

Another object is to reduce incorrect sample analyses resulting from incorrect calibration of a system analyzing the sample.

Another object of the invention is to provide means for increasing the maximum number of calibration information that can be placed on a calibration label of a predetermined size.

Another object is to provide means for supplying auto-calibration data for sensors to two or more instruments adapted to use the sensors. A further object is to provide the data corresponding to each instrument on a common substrate. Yet a further object is to provide the common substrate in a removably attachable form that may be attached to existing sensor packages.

Another object is to provide means for replacing existing (current) auto-calibration labels with labels comprising dual program numbers, where each number is associated with a different instrument.

Another object is to provide improved printing methods for encoding information.

Another objective is to provide means for isolating conductive data. A further object is to increase the amount of data provided in a predefined area, such as a calibration area of a sensor package. A still further object is to increase the quantity of information provided by printing information on a single level as well as on multiple levels.

An object related to multiple layer printing is to print information corresponding to two or more applications on a single layer. Another object is to print information corresponding to one application across multiple layers, i.e., part of the information is on one level and another part is on another level. A further object is to combine techniques for printing a single layer corresponding to multiple applications with techniques for printing multiple layers corresponding to a single application.

Another object is to provide processes for improving results associated with glucose monitoring. A similar object is to provide processes for improving cholesterol monitoring. A more general objective is to provide process for improving analyte level determination.

Other objects and advantages will be apparent to those of ordinary skill in the art from the teachings herein.

BRIEF DESCRIPTION OF THE DRAWINGS

FIG. 1 shows a prior art sensing instrument.
FIG. 2 shows the interior of the sensing instrument of FIG. 1.
FIG. 3 shows a prior art sensor package for use with the sensing instrument shown in FIG. 2.

DESCRIPTION OF ILLUSTRATIVE EMBODIMENTS

Figure 4:
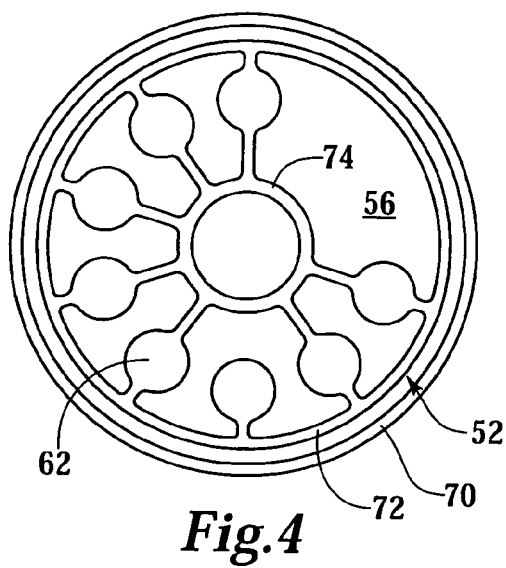
FIG. 4 shows a first print layer of a label in accordance with the invention.
Figure 5:
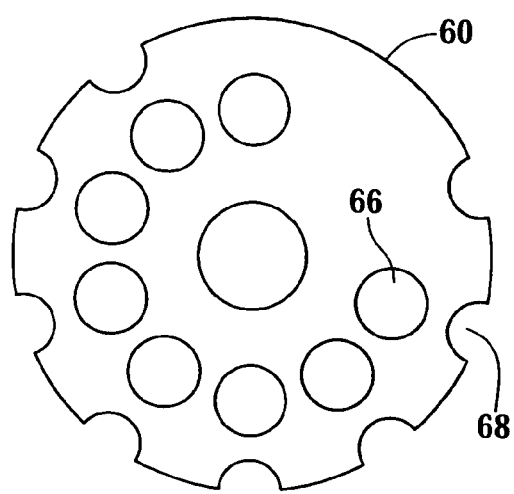
FIG. 5 shows an insulating layer that will overlay the first print layer.
Figure 6:
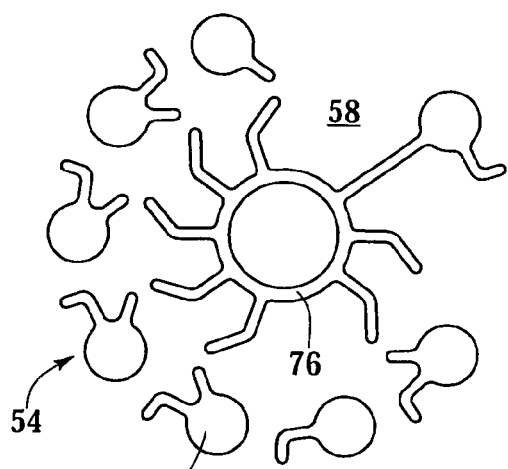
FIG. 6 shows a second print layer that will overlay the insulating layer.

The prior art discloses a method and apparatus for calibrating a sensor instrument. The sensor is used in a sensor system that includes a sensor meter, a sensor for receiving a user sample to be analyzed and a processor for performing a predefined test sequence for measuring a predefined parameter value. A memory is coupled to the processor for storing predefined parameter data values. An auto-calibration code is associated with the sensor and read by the processor before the user sample to be measured is received. The auto-calibration code is used in measuring the predefined parameter data value to compensate for different characteristics of sensors which will vary on a batch to batch basis. Variations of this process will be apparent to those of ordinary skill in the art from the teachings disclosed herein, including but not limited to, the drawings and the claims.

Referring now to FIGS. 1-3, a prior art sensor meter 10 is illustrated. In FIG. 2, the inside of the sensor meter 10 is shown without a sensor package. An exemplary sensor package generally designated by the reference character 12 is separately illustrated in FIG. 3. Sensor meter base member 14 supports an auto-calibration plate 16 and a predetermined number of auto-calibration pins 18, for example, ten auto-calibration pins 18, as shown. The auto-calibration pins 18 are connected for engagement with the sensor package 12. Sensor package 12 carries an auto-calibration label generally designated by the reference character 20. The pins 18 couple with the label 20 when the meter 10 is closed.

Calibration codes assigned for use in the clinical value computations to compensate for manufacturing variations between sensor lots are encoded upon label 20. Label 20 is associated with sensor package 12 comprising of sensors 22. The calibration encoded label 20 is inserted into the instrument 10 with the package 12 of multiple sensors 22 which are stored in individual blisters 24 and read by associated sensor electronic circuitry before one of the sensors 22 is used. Calculation of the correct test values, such as, glucose values from electrical current readings, is based upon solving a single equation. Equation constants based on a calibration code are identified, such as by either using an algorithm to calculate the equation constants or retrieving the equation constants from a lookup table for a particular predefined calibration code which is read from the calibration encoded label 20. The calibration encoded label 20 can be implemented by digital, mechanical, analog, optical or a combination of these techniques.

Referring to FIG. 3, the sensor package 12 is used in a sensor meter 10 for handling of a plurality of sensors 22 which are preferably fluid sensors. The sensor package 12 includes a plurality of sensor cavities or blisters 24 extending toward a peripheral edge of the sensor package 12. Each sensor cavity 24 accommodates one of the plurality of fluid sensors 22. The sensor package 12 is generally circular in shape with the sensor cavities 24 extending from near the outer peripheral edge toward and spaced apart from the center of the sensor package 12.

The sensor package 12 includes an auto-calibration data area generally designated by 26 providing auto-calibration encoded information. This auto-calibration encoded information is provided on the auto-calibration label 20. The label includes a plurality of contact pads 28 aligned for electrical contact engagement with the auto-calibration pins 18 when the sensor package 12 is received within the sensor meter 10. The auto-calibration label 20 includes an inner conductive path or trace 30 and an outer conductive path 32. As described in detail below, selected contact pads 28 are connected to the conductive paths 30 and 32. The auto-calibration pins 18 electrically couple with the label pads 28 on the auto-calibration label 20 when a cover 38 of the meter 10 is closed and a label 20 is present.

In accordance with a feature of the invention, the calibration encoded label 20 is used to automate the process of information transfer about the lot specific reagent calibration assignment for associated sensors 22 such that the sensors 22 can be used with different meters. The calibration codes on a particular label 20 can also be used to distinguish between several types of sensors 22.

The calibration encoded label 20 can be constructed by screenprinting conductive ink onto a base substrate, that can either be a separate substrate (not shown) or the sensor package surface 40. A separate substrate can be attached to the sensor package 12 using an adhesive, such as either a hot melt, UV-cure or fast-curing adhesive. A conductive ink defining calibration encoded label 20 preferably is a carbon, silver or a carbon/silver blended ink. The substrate 12 is any print receptive surface including paper, polymer-filled paper or polymer substrate, preferably a heat stabilized polyethyleneteraphthalate (PET) or polycarbonate.

When the calibration level has been determined, the digital calibration encoded labels 20 are marked by cutting the appropriate traces. It is to be understood that the digital calibration encoded labels 20 can be encoded by printing labels without the appropriate traces to the inner ring 30 or outer ring 32.

With reference to FIGS. 4-7, one embodiment is directed toward an auto-calibration label 50 adapted for use with a first instrument 10, a second instrument (not shown) distinct from the first instrument 10 and a sensor 22 operable with both the first instrument 10 and the second instrument. It will be understood that a sensor package 12 containing the sensor 22 may comprise one or more sensors operable with one or both instruments. Where the sensors in a package 12 have essentially the same calibration characteristics, calibrating an instrument 10 for one of the sensors 22 is effective to calibrate the instrument 10 for all of the sensors 22 in that particular package 12.

In one embodiment, the auto-calibration label 50 comprises first-instrument encoded calibration information 52 that corresponds to the sensor 22 and is adapted to be utilized by the first instrument 10 to auto-calibrate. The first instrument 10 is thereby calibrated for use with the sensor 22. The label 50 also comprises second-instrument encoded calibration information 54 corresponding to the sensor 22. Encoded calibration information 54 is adapted to be utilized by the second instrument to auto-calibrate, whereby the second instrument is calibrated for use with the sensor 22. The second-instrument encoded calibration information 54 is typically distinct from the first-instrument encoded calibration information 52 to account for different calibration characteristics among the two or more instruments 10.

It will be understood, however, that use of distinct in this context may only mean that the encoded information is distinct, but the decoded information is essentially the same. For example, the instruments 10 may have essentially the same calibration characteristics, but the contacts, e.g., pins 18, to couple with the encoded information are located in different places for each instrument 10. Accordingly, the encoded information 52 and 54 corresponding to each instrument 10 is distinct because the encoded information must be arranged to couple with the appropriate instrument. Also the encoded information may convey different sensor characteristics.

The first-instrument encoded calibration information 52 may be defined by a first conductive ink pattern 56. Similarly, the second-instrument encoded calibration information 54 may be defined by a second conductive ink pattern 58, which is preferably electrically isolated from the first pattern 56. For some applications, the second-instrument encoded calibration information 54 is defined in part by the first encoded information 52. For example, the second-instrument encoded information 54 may be defined by the first ink pattern 56 and another pattern that collectively forms the second ink pattern 58. Variations of these processes will be apparent to those of ordinary skill in the art according to particular applications.

Figure 7:
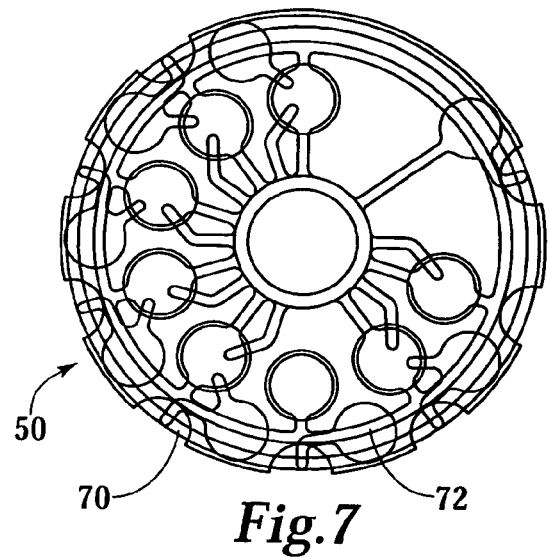
FIG. 7 shows the layers illustrated in FIGS. 4-6 combined to form a final label.

An insulating layer 60, preferably comprising a dielectric, may be used to isolate the first pattern 56 from the second pattern 58. Alternatively, the patterns 56 and 58 may be arranged such that they are not contacting each other. A combination printing technique using the insulating layer 60 and non-contacting patterns is, however, the preferred approach. FIG. 7 illustrates the final label 50 after printing the first pattern 56, then the insulating layer 60 and then the second pattern 58. It is to be understood that the final label is not limited to two layers of conductive ink patterns. It is also to be understood that the first pattern 56 and the second pattern 58 can each be printed across multiple levels; part of a pattern may be at one level while another part is at a different level.

In one embodiment, the first pattern 56 comprises one or more electrical contacts 62 located to couple the first pattern 56 with the first instrument 10 when the label 50 is positioned to be used by the first instrument 10. Similarly, the second pattern 58 comprises one or more electrical contacts 64 located to couple the second pattern 58 with the second instrument when the label 50 is positioned to be used by the second instrument. The insulating layer 60 is adapted to insulate the first pattern 56 from the second pattern 58 while allowing the electrical contacts 62 of the first pattern 56 to couple with the first instrument 10 when the label 50 is positioned in the first instrument 10. Similarly, the insulating layer 60 can also be adapted to insulate the patterns from each other while allowing the electrical contacts 64 of the second pattern 58 to couple with the second instrument when the label 50 is positioned in the second instrument.

For some applications, the insulating layer 60 and the first pattern 56 are preferably adapted to allow the first pattern 56 to be utilized by the first instrument 10 while preventing the second instrument from utilizing or coupling with the first pattern 56. The second pattern 58 and the insulating layer 60 are similarly adapted to allow the second pattern 58 to be utilized with the second instrument while preventing the first instrument 10 from coupling with the second pattern 58. The insulating layer 60 has, in a preferred environment, predefined cut-outs 66 allowing first pattern 56 pads 62 to couple with the first instrument 10. Cut-outs 68 similarly allow second pattern 58 pads 64 to couple with the second instrument.

Another embodiment is directed toward a sensor package 12 comprising one or more sensors 22 operable with the first and second instrument. The package 12 further comprises an auto-calibration label 50 comprising first-instrument encoded calibration information 52 and second-instrument encoded calibration information 54. In one embodiment the sensors 22 are arranged around the label 50 and extended radially from about an area 26 containing the label 50. An insulating layer 60 is disposed over the first-instrument encoded calibration information 52. And the second-instrument encoded calibration information 54 is disposed over the insulating layer 60.

It will be understood that disposing the second-instrument encoded calibration information 54 over the insulating layer 60 does not require all of the information 54 be over the layer 60. For example, a portion 70 of the information 54 corresponding to the second instrument may be disposed contemporaneously with, and on the same level as, information 52 corresponding to the first instrument 10. Similarly, requiring the insulating layer 60 to be between the first 52 and second 54 information does not require the insulating layer 60 to be between all of the first 52 and all of the second 54 information. For example, the second encoded information 54 may be isolated from the first encoded information 52 by printing the information 52 and 54 such that the patterns are separated. For example, an outer ring 70 of the second encoded information 54 may be printed outside of and separated from an outer ring 72 of the first encoded information 52. From the teachings herein, including those teachings of U.S. Pat. No. 5,856,195, which is incorporated herein by reference in its entirety, it will be apparent to those of ordinary skill in the art that a variety of sensor means and auto-calibration means are combinable in accordance with the teachings herein.

In the illustrated embodiment depicted in FIGS. 4-7, the first print pattern comprises an inner ring 74 and the second print pattern comprises an inner ring 76. For some applications, the inner rings 74 and 76 represent logical 0s and the outer rings 72 and 70 represent logical 1s. The traces connecting the inner rings 74 and 76 with the outer rings 72 and 70 are cut to provide binary code which is readable by the one or more instruments 10. Calibration information corresponding to the 22 may thus be provided to the instrument 10.

Use of positional terms such as "above" and "below" are merely used to facilitate description and understanding of the illustrated embodiments and claimed invention. It will be understood by those of ordinary skill in the art that the terms are relative and not to be construed to limit the claims in an absolute frame of reference. For example, if a label comprising a first layer "under" a second layer is turned over, the second layer is, in an absolute frame of reference, now under the first layer. But in a relative frame, the first layer is still under the second, regardless of the orientation of the label. Similarly, requiring a layer to be between two layers does not require three levels of printing, where only one layer is printed on a given level.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the claimed invention, which is set forth in the following claims.

What is claimed is:

1. An auto-calibration label comprising:
   first encoded calibration information corresponding to a first sensor, wherein the first information is configured to be used by a first instrument to auto-calibrate, whereby the first instrument is calibrated for the first sensor; and
   first additional encoded calibration information corresponding to a second sensor, wherein the additional information is distinct from the first information and is configured to be used by a second instrument different from the first instrument to auto-calibrate, whereby the second instrument is calibrated for the second sensor.

2. The label of claim 1, comprising second encoded calibration information corresponding to the second sensor, wherein the second information corresponding to the second sensor is configured to be use by the first instrument to auto-calibrate such that the first instrument is calibrated for the second sensor and the second information corresponding to the second sensor is at least equivalent to the first information corresponding to the first sensor.

3. The label of claim 2, wherein the first information corresponding to the first sensor is the same as the second information corresponding to the second sensor and the second information is distinct from the additional information.

4. The label of claim 1, wherein the first information corresponding to the first sensor also corresponds to the second sensor.

5. The label of claim 1, wherein the additional information overlays the first information.

6. The label of claim 5, wherein the additional information overlays the first information such that the first instrument is configured to utilize the first information without using the additional information and the second instrument is configured to utilize the additional information without using the first information.

7. The label of claim 5, further comprising an insulating layer located between the first information and the additional information.

8. The label of claim 1, comprising:
a first conductive ink pattern defining the first information that is configured to be used by the first instrument; and
a second conductive ink pattern defining the additional information that is configured to be used by the second instrument.

9. The label of claim 8, wherein:
the first conductive ink pattern comprises one or more electrical contacts located to couple the first pattern with the first instrument when the label is positioned to be utilized by the first instrument; and
the second conductive ink pattern comprises one or more electrical contacts located to couple the second pattern with the second instrument when the label is positioned to be utilized by the second instrument.

10. The label of claim 9, further comprising an insulating layer being located between the first conductive ink pattern and the second conductive ink pattern.

11. The label of claim 10, wherein the insulating layer comprises a dielectric.

12. The label of claim 10, wherein:
the first conductive ink pattern comprises inner and outer rings; and
the second conductive ink pattern comprises inner and outer rings.

13. The label of claim 12, wherein the insulating layer is located between the ink patterns, and wherein the inner and outer rings of the first pattern are below the insulating layer and the outer ring of the second pattern is below the insulating layer.

14. An auto-calibration label configured for use with a first instrument, a second instrument distinct from the first instrument and a sensor operable with both the first instrument and the second instrument, the label comprising:
first instrument encoded calibration information corresponding to the sensor and configured to be used by the first instrument to auto-calibrate such that the first instrument is calibrated for use with the sensor; and
second instrument encoded calibration information corresponding to the sensor and configured to be used by the second instrument to auto-calibrate such that the second instrument is calibrated for use with the sensor, wherein the second instrument encoded calibration information is distinct from the first instrument encoded calibration information.

15. The label of claim 14, comprising:
a first conductive ink pattern defining the first instrument encoded calibration information; and
a second conductive ink pattern defining the second instrument encoded calibration information.

16. The label of claim 15, wherein the first pattern is electronically isolated from the second pattern.

17. The label of claim 15, further comprising an insulating layer located between the first and the second pattern, wherein:
the first pattern comprises one or more electrical contacts located to couple the first pattern with the first instrument when the label is positioned to be used by the first instrument;

the second pattern comprises one or more electrical contacts located to couple the second pattern with the second instrument when the label is positioned to be used by the second instrument; and
the insulating layer is configured to insulate the first pattern from the second pattern while allowing the electrical contacts of the first pattern to couple with the first instrument and allowing the electrical contacts of the second pattern to couple with the second instrument.

18. The label of claim 17, wherein:
the insulating layer and the first pattern are configured to allow the first pattern to be utilized by the first instrument while preventing the second instrument from utilizing the first pattern; and
the insulating layer and the second pattern are configured to allow the second pattern to be utilized by the second instrument while preventing the first instrument from utilizing the second pattern.

19. A sensor package adapted for use with a first instrument and a second instrument, the sensor package comprising:
one or more sensors operable with the first instrument and the second instrument; and an auto-calibration label comprising:
first instrument encoded calibration information corresponding to the one or more sensors and configured to be used by the first instrument to auto-calibrate such that the first instrument is calibrated for use with the one or more sensors, and
second instrument encoded calibration information corresponding to the one or more sensors and configured to be used by the second instrument to auto-calibrate such that the second instrument is calibrated for use with the one or more sensors, wherein
the second instrument encoded calibration information is distinct from the first instrument encoded calibration information.

20. The package of claim 19, comprising one or more blisters respectively containing the one or more sensors, wherein the blisters are arranged around the auto-calibration label.

21. The package of claim 19, wherein the auto-calibration label comprises an insulating layer between the first instrument encoded calibration information and the second encoded calibration information.

22. The package of claim 21, wherein the second instrument encoded calibration information and the first instrument encoded calibration information are layered with the insulating layer positioned therebetween.

23. The package of claim 19, comprising:
a first conductive ink pattern defining the first instrument encoded calibration information and comprising one or more electrical contacts respectively associated with the one or more sensors and being located to couple the first conductive ink pattern with the first instrument without coupling the first conductive ink pattern to the second instrument; and
a second conductive ink pattern defining the second instrument encoded calibration information and comprising one or more electrical contacts respectively associated with the one or more sensors and being located to couple the second conductive ink pattern with the second instrument without coupling the second conductive ink pattern to the first instrument.

24. The package of claim 23, wherein the first conductive ink pattern is isolated from the second conductive ink pattern.

25. The package of claim 23, wherein the auto-calibration label comprises an insulating layer isolating the first conductive ink pattern from the second conductive ink pattern.

26. The package of claim 25, wherein the insulating layer comprises predetermined cut-outs to selectively allow coupling between the first conductive ink pattern and the first instrument while preventing coupling between the second conductive ink pattern and the first instrument.

27. A sensor package for use in a first instrument configured to determine an analyte concentration in a sample and a second instrument configured to determine an analyte concentration in the sample, the package comprising:
one or more sensors for receiving the sample and being operable with the first instrument and the second instrument; and
an auto-calibration label comprising:
first instrument encoded calibration information corresponding to the one or more sensors and configured to be used by the first instrument to auto-calibrate such that the first instrument is calibrated for use with the one or more sensors to enable the first instrument to determine an analyte concentration in the sample received by the one or more sensors, and
second instrument encoded calibration information corresponding to the one or more sensors and configured to be used by the second instrument to auto-calibrate such that the second instrument is calibrated for use with the one or more sensors to enable the second instrument to determine an analyte concentration in the sample received by the one or more sensors,
wherein the second instrument encoded calibration information is separated and distinct from the first instrument encoded calibration information.

28. The package of claim 27, wherein the label further comprises an insulating layer between the first instrument information and the second instrument information.

29. The package of claim 28, wherein the label comprises:
a first conductive ink pattern defining the first instrument encoded calibration information; and
a second conductive ink pattern defining the second instrument encoded calibration information.

30. The package of claim 29, wherein the first conductive ink pattern, the insulating layer, and the second conductive ink pattern are layered.

31. The package of claim 27, wherein the one or more sensors are substantial identical.

32. A sensor package configured for use with a plurality of predetermined instruments adapted to determine at least one of a plurality of predefined parameter values associated with a sample, the package comprising:
one or more sensors operable with the instruments to receive a sample;
a calibration information area;
first instrument encoded calibration information located in the area, the information being configured to be used by a first of the plurality of instruments to auto-calibrate such that the first instrument is calibrated for use with at least one of the one or more sensors to enable the first instrument to determine at least one of the predefined parameter values associated with a sample; and
second instrument encoded calibration information located in the area, the information being configured to be used by a second of the plurality of instruments to auto-calibrate such that the second instrument is calibrated for use with at least one of the one or more sensors to enable the second instrument to determine at least one of the predefined parameter values associated with a sample wherein the second encoded calibration information is distinct from the first encoded calibration information.

33. The sensor package of claim 32, wherein:
the first instrument encoded calibration information is prevented from being utilized by the second instrument; and
the second instrument encoded calibration information is prevented from being utilized by the first instrument.

34. The sensor package of claim 33, wherein:
the first instrument encoded calibration information is prevented from coupling with the second instrument; and
the second instrument encoded calibration information is prevented from coupling with the first instrument.

35. The sensor package of claim 32, comprising:
a first conductive ink pattern defining the first instrument encoded information;
a second conductive ink pattern defining the second instrument encoded information.

36. The sensor package of claim 35, wherein each conductive ink pattern comprises one or more electrical contacts respectively associated with the one or more sensors and wherein the one or more electrical contacts of each pattern are arranged to couple with the instrument corresponding to the encoded information defined by the pattern.

37. The sensor package of claim 36, wherein the second instrument encoded calibration information and the first instrument encoded information carry similar calibration characteristic information.

38. The sensor package of claim 35, comprising an insulating layer between the first and second patterns, wherein the first and second patterns are layered.

39. An auto-calibration label comprising:
a first conductive ink pattern defining first encoded calibration information configured to be used by a first instrument to auto-calibrate the first instrument;
a second conductive ink pattern overlaying the first conductive ink pattern and defining second encoded calibration information configured to be used by a second instrument to auto-calibrate the second instrument; and
an insulating layer located between the first ink pattern and the second ink pattern, wherein the second encoded calibration information is distinct from the first encoded calibration information.

40. A method of manufacturing an auto-calibration label, the method comprising the acts of:
printing a first conductive ink pattern layer comprising encoded calibration information on a substrate wherein the encoded calibration information of the first pattern is configured to be used by a first instrument to auto-calibrate the first instrument;
printing an insulating layer over the first conductive ink pattern so as to isolate the first conductive ink pattern; and
printing a second conductive ink pattern comprising encoded calibration information
over the insulating layer such that the second conductive ink pattern is isolated from the first conductive ink pattern,
wherein the encoded calibration information of the second pattern is configured to be used by a second instrument to auto-calibrate the second instrument, and wherein the first instrument and calibration information of the first pattern are distinct from the second instrument and calibration information of the second pattern.

41. The method of claim 40, comprising printing a portion of the second conductive ink pattern while printing the first conductive ink pattern.

42. A method of manufacturing a sensor package comprising the acts of:
- supporting one or more sensors by a substrate;
- applying to the substrate calibration information corresponding to the one or more sensors and a first instrument configured to be used the one or more sensors; and
- applying to the substrate calibration information corresponding to the one or more sensors and a second instrument configured to be used the one or more sensors, the first instrument and the calibration information corresponding to the first instrument being distinct from the second instrument and the calibration information corresponding to the second instrument.

43. The method of claim 42, comprising applying the calibration information corresponding to the second instrument in an area of the substrate containing the calibration information corresponding to the first instrument.

44. The method of claim 42, comprising applying a label to the substrate wherein the label comprises the calibration information corresponding to the first and second instruments.

45. The method of claim 44, comprising positioning the label in a predefined area of the substrate.

* * * * *